(12) United States Patent
Berge (10) Patent No.: US 8,206,739 B2
(45) Date of Patent: Jun. 26, 2012

(54) FISH PROTEIN HYDROLYZATE

(75) Inventor: Rolf Berge, Bønes (NO)

(73) Assignee: Atlantic Garden AS, Storebo (NO)

( * ) Notice: Subject to any disclaimer, the term of this patent is extended or adjusted under 35 U.S.C. 154(b) by 271 days.

(21) Appl. No.: 10/563,272

(22) PCT Filed: Jul. 2, 2004

(86) PCT No.: PCT/NO2004/000202
§ 371 (c)(1),
(2), (4) Date: Jul. 24, 2006

(87) PCT Pub. No.: WO2005/002605
PCT Pub. Date: Jan. 13, 2005

(65) Prior Publication Data
US 2007/0142274 A1    Jun. 21, 2007

(30) Foreign Application Priority Data
Jul. 4, 2003   (NO) .................................. 20033078

(51) Int. Cl.
*A61K 47/00* (2006.01)
(52) U.S. Cl. ....... 424/439; 435/68.1; 514/1.9; 514/14.9; 514/16.4
(58) Field of Classification Search ........................ None
See application file for complete search history.

(56) References Cited

U.S. PATENT DOCUMENTS
2002/0182290 A1 * 12/2002 Nielsen ............................. 426/56

OTHER PUBLICATIONS

Bergeron et al., Journal of Nutrition, 1992, vol. 122, p. 1731-1737.*
Kristisson & Rasco, Critical Reviews in Food Science and Nutrition, 2000, vol. 40, No. 1, p. 43-81.*
Sharma et al., Bioresource Technology, 2002, vol. 85, p. 327-329.*
Pena-Ramos et al., Journal of Food Science, 2002, vol. 67, No. 8, p. 2952-2956.*
Aoyama et al., Biosci Biotechnol. Biochem., 2000, vol. 64, No. 12, p. 2594-2600.*
Bergeron et al., Journal of Nutrition, 1992, vol. 122, p. 1731-1737.*
Liceaga-Gesualdo et al., Journal of Food Science, 1999, vol. 64, No. 6, p. 1000-1004.*
Ji et al., Gastroenterology, My 2003, vol. 124, p. 1488-1499.*
Cahu et al., Aquaculture, 2001, vol. 200, p. 161-180.*
Van Guldener & Stehouwer, Expert Opin. Pharmacother. 2001, vol. 2, No. 9, p. 1449-1460.*
Oliveira et al., Nutrition Journal, 2003, vol. 2, p. 1-5.*
Bobe et al. J Dairy Sci. 2004, vol. 87, p. 3105-3124.*
Liaset et al. Process Biochemistry, 2002, vol. 37, p. 1263-1269.*

* cited by examiner

*Primary Examiner* — Kade Ariani
(74) *Attorney, Agent, or Firm* — Dobe Law Group, LLC; Christopher Aniedobe

(57) ABSTRACT

The present invention relates to the use of a enzyme treated fish protein hydrolyzate (FPH). The FPH material lowers the concentration of cholesterol in plasma, and triglycerides in the liver. FPH also induces a favorable change in the fatty acid pattern, and lowers the concentration of homocysteine in plasma. A preferable embodiment of the invention relates to the use of FPH as an anti-atherogenic and cardio protective agent, either given as a pharmaceutical or as a functional food.

16 Claims, 4 Drawing Sheets

FISH PROTEIN HYDROLYZATE

This application is a 371 of Application No. PCT/NO04/00202 filed on Jul. 2, 2004.

FIELD OF INVENTION

The present invention relates to the use of an enzyme treated fish protein hydrolyzate (FPH). The FPH material lowers the concentration of cholesterol in plasma, and triglycerides in the liver. FPH also induces a favourable change in the fatty acid pattern, and lowers the concentration of homocysteine in plasma. A preferable embodiment of the invention relates to the use of the FPH material as an anti-atherogenic and cardio protective agent, either given as a pharmaceutical or as a nutritional composition, e.g. as a functional food.

BACKGROUND OF THE INVENTION

The fish farming industry has grown enormously both in Norway and world-wild during the recent years, especially Salmon. Much of the fish are sold to the consumer as gutted, whole fish, but significant amounts are sold as fillets. Only 50-70% of the salmon is fillets, whereas the rest is sold as low-valued products such as fish meal and fish ensilage.

Through enzymatic treatment the fish meat and also the fish frames can be separated into an aqueous fraction rich in proteins, called fish protein hydrolysate (FPH). The enzymatic hydrolysing process is highly controllable, and the products are reproducible and well defined.

Surprisingly, the present inventors have shown that the fish protein hydrolysate (FPH) in accordance with the invention has several beneficial biological effects, and that such a material can be used as a pharmaceutical or nutritional material.

We have shown that the FPH lowers the concentration of plasma cholesterol and homocysteine, and also lowers the concentration of hepatic triacylglycerols. Based on these findings, it is anticipated that the FPH will have a preventive and/or therapeutic effect on stenosis, atherosclerosis, coronary heart disease, thrombosis, myocardial infarction, stroke and fatty liver. Treatment with a fish protein material represents a new way to treat these diseases.

The FPH is especially useful as a functional protein in food products, particularly when used as a substitute for natural plasma in animal feeds and in pet foods. When used in pet foods, additional ingredients may be added to the product such as fats, sugars, salt, flavourings, minerals, etc. The product may then be formed into chunks resembling natural meat chunks in appearance and texture. The product of the invention has the further advantages that this is readily formulated to contain necessary nutrients, is easily digested by the animals and is palatable to the animals.

DETAILED DESCRIPTION OF THE INVENTION

The present invention relates to a FPH for the preparation of a pharmaceutical or nutritional preparation for the treatment and/or prevention of atherosclerosis, coronary heart disease, stenosis, thrombosis, myocardial infarction, stroke and fatty liver.

The experimental data clearly shows that the FPH according to the invention lowers the concentration of homocysteine in plasma. Homocysteine is a risk factor in diseases such as atherosclerosis, coronary heart disease, stenosis, thrombosis, myocardial infarction and stroke, and it is thus anticipated the FPH material of the invention will be effective in preventing and treating of these diseases.

The data also shows that the level of triacylglycerols in the liver is decreased by administration of FPH, and it is anticipated that the FPH material can be used for the treatment and prevention of fatty liver.

A further embodiment of the present invention relates to a FPH for the preparation of a pharmaceutical or nutritional composition for the treatment and/or prevention of hypercholesterolemia, as we have shown that said material is capable of lowering the plasma concentration of cholesterol.

A still further embodiment relates to the use of a FPH for the preparation of a pharmaceutical or nutritional composition for lowering the concentration of homocysteine in the plasma. A hyperhomocysteine level can be established before the above indicated diseases are manifested. The administration of the FPH material has a general homocysteine lowering effect, and the material of the present invention is thus especially suited for preventing the onset of, and lowering the risk for the above indicated diseases.

The results further indicate that the FPH material has general cardio and artery protective features, and we anticipate that the material can be given to decrease the risk for artery and cardio related diseases.

An object of the present invention is to administer the FPH material either as a prophylactic or pharmaceutical drug, or as a functional feed or food material. The material can be given to human and non-human animals.

A preferred embodiment of the invention relates to a feed material comprising the fish protein hydrolysate. The material can be used for feeding agricultural animal, such as gallinaceous birds, bovine, ovine, caprine or porcine mammals, domestic or pet animal, such as dog or cat, and fish or shellfish, such as salmon, cod, Tilapia, clams, oysters, lobster or crabs.

A preferred embodiment of the invention uses FPH material produced by an enzymatic treatment of fish meat or frames. Preferable the enzyme composition Protamex™ is used, and the fish is preferable salmon.

DEFINITIONS USED IN THE APPLICATION

Animals

In this context the term "animals" include mammals such as humans and farm (agricultural) animals, especially the animals of economic importance such as gallinaceous birds; bovine, ovine caprine and porcine mammals, especially those that produce products suitable for the human consumption, such as meat, eggs and milk. Further, the term is intended to include fish and shellfish, such as salmon, cod, Tilapia, clams and oysters. The term also includes domestic animals such as dogs and cats.

Treatment

In relation to the pharmaceutical applications of the invention the term "treatment" refers to a reduction of the severity of the disease.

Prevention

The term "prevention" refers to the preventing of a given disease, i.e. a compound of the present invention is administered prior to the onset of the condition. This means that the compounds of the present invention can be used as prophylactic agents or as ingredients in functional foods or feed in order to prevent the risk or onset of a given disease.

FPH-Enzyme Treated Fish Protein Hydrolysate

The FPH material is a protein hydrolysate resulting from an enzymatic treatment of a fish material. The FPH material contains high proportions of proteins and peptides.

Administration of the Compounds of the Present Invention

As a pharmaceutical medicament the compounds of the present invention may be administered directly to the animal by any suitable technique, including parenterally, intranasally, orally, or by absorption through the skin. They can be administered locally or systemically. The specific route of administration of each agent will depend, e.g., on the medical history of the animal. The preferred administration route is orally.

Examples of parenteral administration include subcutaneous, intramuscular, intravenous, intraarterial, and intraperitoneal administration If given continuously, the compounds of the present invention are each typically administered by 1-4 injections per day or by continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner.

For parenteral administration, in one embodiment, the compounds of the present invention are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the compounds of the present invention each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier may suitably contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins, chelating agents such as EDTA: sugar alcohols such as manitol or sorbitol; counterions such as sodium; and/or non-ionic surfactants such as polysorbates, poloxamers, or PEG.

For oral pharmacological compositions such carrier material as, for example, water, gelatine, gums, lactose, starches, magnesium-stearate, talc, oils, polyallcene glycol, petroleum jelly and the like may be used. Such pharmaceutical preparation may be in unit dosage form and may additionally contain other therapeutically valuable substances or conventional pharmaceutical adjuvants such as preservatives, stabilising agents, emulsifiers, buffers and the like. The pharmaceutical preparations may be in conventional liquid forms such as tablets, capsules, dragees, ampoules and the like, in conventional dosage forms, such as dry ampulles, and as suppositories and the like.

In addition, the compounds of the present invention are appropriately administered in combination with other treatments for combatting or preventing a specific disease.

The invention will be more fully understood by reference to the following examples. They should not, however, be construed as limiting the scope of the invention.

A preferred embodiment of the present invention relates to a nutritional composition comprising the FPH material which may be formulated in any conventional way to a feed or food product.

Experimental Section

The following non-limiting examples serve to further illustrate the invention.

Chemicals

[I-$^{14}$C] palmitoyl-L-carnitine (54 Ci/mmol) was purchased from Amersham. The chemicals used for real-time RT-PCR was from Applied Biosystems. All other chemicals were obtained from common commercial sources and were of reagent grade.

Fish Protein Hydrolyzate (FPH)

FPH was produced from fish flesh remnants on salmon bone frames after filleting as described in example 1, the Supro 530 EX soy protein was from duPont Protein Technologies (St. Louis, Mo., USA), and bovine casein sodium salt, C-8654, was from Sigma-Aldrich.

Animals and Treatments 4-5 weeks old male obese Zucker rats, Crl:(ZUC)/faBR from Charles River, Germany, averaging 120±3 g at the start of the experiment, were kept in a room maintained at 12 hours light-dark cycles, at a temperature of 20±3° C., and relative humidity of 65±15%. The day after arrival the rats were randomised and placed separately in metabolic cages and divided into three experimental groups, each of six animals. The rats were adapted to the experimental conditions and experimental diets for 4 days, after which the faeces were collected for 7 days. The semipurified diets (Table 1), contained 20% crude protein (N×6.25) in the form of FPH or casein (control).

TABLE 1

Composition of the experimental diets

| g/kg diet | FPH | Casein |
|---|---|---|
| Protein | 233.9 | 217.6 |
| Soybean oil [1] | 100 | 100 |
| Sucrose | 110 | 110 |
| Vitamins [2] | 10 | 10 |
| Minerals [3] | 30 | 30 |

TABLE 1-continued

Composition of the experimental diets

| g/kg diet | FPH | Casein |
|---|---|---|
| Cellulose | 20 | 20 |
| NaCl | — | 21.8 |
| Dextrin | 496.1 | 490.6 |

[1] Fatty acid composition of the soybean oil (g/100 g fat): 18:2n – 6 (54.1 ± 0.5), 18:1n – 9 (21.8 ± 0.2), 16:0 (11.2 ± 0.1), 18:3n – 3 (6.1 ± 0.2), 18:0 (3.7 ± 0.1), 18:1n – 7 (1.5 ± 0.1), 20:0 (0.5 ± 0.1), 22:0 (0.5 ± 0.1).
[2] Vitamins (mg/kg diet): 8 mg vit.A (4000 I.U.), 2 mg vit.D3 (1000 I.U.), 60 mg vit.E (30 I.U.), 0.1 mg vit.K (0.05 I.U.), 1000 mg choline hydrogentartrate, 4 mg thiamine, 3 mg riboflavin, 6 mg pyridoxine, 20 mg niacin, 8 mg Ca-pantothenat, 1 mg folin, 5 mg vit.B12 (0.05 I.U.).
[3] Minerals (g/kg diet): 8.5 g $CaCO_3$, 6.2 g $CaHPO_4 \times 2H_2O$, 12.3 g $KH_2PO_4$, 1.4 g $MgCO_3$, 0.4 $NaCO_3$, 0.8 g NaCl, 0.02 g $CuSO_4 \times 5H_2O$, 0.002 g NaF, 0.0002 g KI, 0.2 g $FeSO_4 \times H_2O$, 0.05 g $ZnSO_4 \times H_2O$.

The animals were daily offered equal feed rations, which were adjusted to meet the demand of the growing animal. The animals had free access to tap water. The rats were fed for 22 or 23 days after acclimatisation (three rats from each group were killed on day 22 and the rest on day 23), and the body weight was measured weekly. At the end of the feeding period, the animals were anaesthetised subcutaneously by 1:1 Hypnorm®/Dormicum® (Fentanyl/fluanisone-Midazolam), 0.2 mL/100 g body weight. Cardiac puncture was performed to collect blood samples (in heparin), and the liver was dissected. Parts of the liver were immediately frozen in liquid $N_2$, while the rest of the liver was chilled on ice for homogenisation. The protocol was approved by the Norwegian State Board of Biological Experiments with Living Animals.

Preparation of Subcellular Fractions

Livers from the rats were homogenised individually in ice-cold sucrose-solution (0.25 mol/L sucrose in 10 mmol/L HEPES buffer pH 7.4 and 1 mmol/L EDTA) using a Potter-Elvehjem homogeniser. The subcellular fractions were isolated as described in Berge, R. K. et al (Berge, R. K., Flatmark, T. & Osmundsen, H. (1984), Enhancement of long-chain acyl-CoA hydrolase activity in peroxisomes and mitochondrial of rat liver by peroxisomal proliferators. Eur J Biochem 141: 637-644). Briefly, the homogenate was centrifuged at 1 000×g for 10 min to separate the post-nuclear from the nuclear fraction. A mitochondrial-enriched fraction was prepared from the post-nuclear fraction at 10 000×g for 10 min. A peroxisome-enriched fraction was prepared by centrifugation of the post-mitochondrial fraction at 23 500×g for 30 min. A microsomal-enriched fraction was isolated from the post-peroxisomal fraction at 100 000×g for 73 min. The remaining supernatant was collected as the cytosolic fraction. The procedure was performed at 0-4° C., and the fractions were stored at −80° C. Protein was assayed using the BioRad protein assay kit (BioRad, Heraules, Calif.) and bovine serum albumine as standard.

Enzyme Assays

Carnitine palmitoyltransferase I (CPT-I) activity was measured essentially as described by Bremer (Bremer, J. (1981) The effect of fasting on the activity of liver carnitine palmitoyltransferase and its inhibition by malonyl-CoA. Biochim Biophys Acta 665: 628-631). The assay for CPT-I contained 20 mmol/L HEPES pH 7.5, 70 mmol/L KCl, 5 mmol/L KCN, 100 μmol/L palmitoyl-CoA, 10 mg BSA/mL, and 0.6 mg tissue protein/mL. The reaction was started with 200 μmol/L [methyl-$^{14}$C] L-carnitine (200 cpm/nmol). Assay conditions for CPT-II were identical except that BSA was omitted and 0.01% Triton X-100 were included. Tissue protein concentration was 2.5 μg/mL. Acyl-coenzyme A cholesterol acyltransferase (ACAT) was measured by using 130 mg protein and $^{14}$C-oleyl-CoA as substrate. The product was separated on TLC plates using hexane:diethylether:acetic acid (80:20:1) as the mobile phase, and counted in a scintillation counter (Win Spectral 1414 liquid scintillation counter, Wallac). 3-Hydroxy-3-methylglutaryl (HMG)-CoA reductase was measured by using 80 mg protein and $^{14}$C-HMG-CoA as a substrate. The product was separated on TLC plates using acetone:benzene (1:1) as the mobile phase, and counted in a scintillation counter. Fatty acid synthase was measured as described by Roncari (Roncari, D. A. (1981) Fatty acid synthase from human liver. Methods Enzymol 71 Pt C: 73-79), modified according to Skorve et al. (Skorve, J., al-Shurbaji, A., Asiedu, D., Bjorkhem, I., Berglund, L. & Berge, R. K. (1993) On the mechanism of the hypolipidemic effect of sulfur-substituted hexadecanedioic acid (3-thiadicarboxylic acid) in normolipidemic rats. J Lipid Res 34: 1177-1185), and acetyl-CoA carboxylase was determined by measuring the amount of $NaH^{14}CO_3$ incorporated into malonyl-CoA.

Lipid Analysis

Lipids in whole liver and heparinised plasma were measured in the Tecnicon Axon system (Miles, Tarrytown, N.Y.), with the Bayer triglyceride and cholesterol enzymatic kits (Bayer, Terrytown, N.Y.) and the PAP 150 phospholipid enzymatic kit (bioMélieux, Lyon, France). Liver lipids were first extracted according to Bligh and Dyer (Bligh, E. G. & Dyer, W. J. (1959) A rapid method of total lipid extraction and purification. Can J BiochemPhysiol 37: 911-91.

Faecal Sterols

Faecal total bile acids were prepared according to Suckling et al. (Suckling, K. E., Benson, G. M., Bond, B., Gee, A., Glen, A., Haynes, C. & Jackson, B. (1991) Cholesterol lowering and bile acid excretion in the hamster with cholestyramine treatment. Atherosclerosis 89: 183-190) with some modifications. Two mL of NABH in ethanol (mg/mL) was added to 0.1 g of powdered dry feces. The mixture was allowed to react for 1 hour at ambient temperature, after which 50 μl of 2 mol/L HCl was added to remove any excess of NABH. Neutral sterols were extracted from the samples with n-hexan (two consecutive washings) before the samples were hydrolysed over night with 200 μl 10 mol/L NaOH at 110° C., 240 μl of the hydrolysate together with 2.8 mL water was applied to Bond Elut $C^{18}$ columns (Varian, 200 mg, 3 mL), that had previously been activated by 3 mL methanol and 3 mL water. Bile acids were retained in the columns, which were washed twice with 3 mL of 20% methanol in water, before the bile acids were eluted with 3 mL of methanol. The bile acids were air-dried at 45° C. and resolved in 1 mL of isopropanol. Total bile acids were determined enzymatically using a total bile acid diagnostic kit (Sigma 450A) on the Tecnicon Axon system.

Amino Acids

Amino acids in the diets were determined after hydrolysis in 6 M HCl at 110±2° C. for 22 hours and pre-derivatisation with phenylisothiocyanate according to the method of Cohen and Strydom (34). Total cysteine in the feeds was determined after oxidation of cysteine and cystine with 9:1 performic acid (88%): $H_2O_2$ (30%) (v/v) to yield cystic acid. The samples were then hydrolysed in 6 M HCl at 110±2° C. for 22 hours and further treated as the amino acid analysis described above. Amino acids in liver and plasma were determined in a Biochrom 20 plus Amino Acid Analyzer (Amersham Pharmacia Biotech, Sweden) equipped with a lithium column with post column ninhydrin derivatization as previously described (24). Prior to analysis, liver samples were extracted and deproteinated by the addition of 2 volumes of 5% sulfosalisylic acid, kept on ice for 30 min and centrifuged at 5 000×g for 15 min. The supernatants were mixed 4:1 (v/v) with internal standard (2.5 mmol/L Norleucine in 0.1 mol/L HCl). Plasma samples were mixed 1:1 with internal standard (1 mmol/L Norleucine in 0.1 mol/L HCl), centrifuged at 10000×g for 5 min before the supernatant was centrifuged in a filter tube (cut off 10 kDa, Biomax PB polyethersulfone membrane, Millipore Corp., USA) at 10000×g for 30 min.

Fatty Acid Composition

Fatty acids were extracted from the samples with 2:1 chloroform: methanol (v/v) (35). The samples were filtered, saponified and esterified in 12% $BF_3$ in methanol (v/v). Fatty acid composition of total lipids from liver and plasma was analysed using methods described by Lie and Lambertsen (Lie, O. & Lambertsen, G. (1991) Fatty acid composition of glycerophospholipids in seven tissues of cod (*Gadus morhua*), determined by combined high-performance, liquid chromatography and gas chromatography. J Chromatogr 565: 119-129). Fatty acid methyl esters were separated using a Carlo Erba gas chromatograph ('cold on column' injection, 69° C. for 20 s, increase at 25° C. $min^{-1}$ to 160° C. and hold at 160° C. for 28 min, increase at 25° C. $min^{-1}$ to 190° C. and hold at 190° C. for 17 min, increase at 25° C. $min^{-1}$ to 220° C. and hold at 220° C. for 9 min) equipped with a 50 m CP-sil 88 (Chrompack, Middelburg, The Netherlands) fused silica capillary column (i.d. 0.32 mm). The fatty acids were identified by retention time using standard mixtures of methyl esters Nu-Chek-Prep, Elyian, Minn., USA). The fatty acid composition (weight percentage) was calculated using an integrator (Turbochrom Navigator, Version 4.0) connected to the GLC.

Lipids were extracted from plasma triacylglycerol-rich lipoprotein fraction using a mixture of chloroform and methanol, and separated by thin layer chromatography on silica gel plates (0.25 mm Silica gel 60, Merck) developed in hexane-diethyl ether-acetic acid (80:20:1, v/v/v) and visualized using Rhodamine 6G (0.05% in methanol, Sigma) and UV light. The spots were scraped off and transferred to tubes containing heneicosanoic acid (21:0) as internal standard. $BF_3$-methanol was added to the samples for transesterification. To remove neutral sterols and non-saponifiable material, extracts of fatty acyl methyl esters were heated in 0.5 mol/L KOH in ethanol-water solution (9:1). Recovered fatty acids were then re-esterified using $BF_3$-methanol. The methyl esters were analyzed on a GC8000Top gas chromatograph (Carlo Erba Instrument), equipped with a flame ionization detector (FID), programmable temperature of vaporization injector, AS 800 autosampler (Carlo Erba Instrument) and a capillary column (60 m×0.25 mm) containing a highly polar SP 2340 phase with film thickness 0.20 μm (Supelco). The initial temperature was 130° C., heating 1.4° C./min to final temperature 214° C. The injector temperature was 235° C. The detector temperature was 235° C., using hydrogen (25 mL/min), air (350 mL/min) and nitrogen as make-up gas (30 mL/min). The samples were run with constant flow using hydrogen as a carrier gas (1.6 mL/min). The splitting ratio was 20:1. The methyl esters were positively identified by comparison to known standards (Larodan Fine Chemicals, Malmo, Sweden) and verified by mass spectrometry. Quantification of the fatty acids was made with Chrom-Card A/D 1.0 chromatography station (Carlo Erba Instruments) based on heneicosanoic acid as an internal standard.

Acyl-CoA-Esters

Acyl-CoA esters in liver were measured by reversed-phase high-performance liquid chromatography. 100 mg frozen liver was homogenised in ice-cold 1.4 mol/L $HClO_4$ and 2 mmol/L D-dithiothleitol to obtain 10% (w/v) homogenate, and centrifuged at 12 000×g for 1 min. 122 μl ice-cold 3 mol/L $K_2CO_3$ with 0.5 mol/L triethanolamine was added to 500 μl of the supernatant. After 10 min on ice, the solution was centrifuged at 12 000×g for 1 min at 4° C. 40 μl of the supernatant was injected onto the high-performance liquid chromatography column, and the acyl-CoA esters were measured according to Demoz et al (39), with the following modifications: elution buffer A was adjusted to pH 5.00, the profile of the gradient elution was as follows: 0 min, 83.5% A; 10 min, 55% A; 17 min, 10% A, and the flow-rate was 1.0 mL/min.

Isolation of Plasma Triacylglycerol-Rich Lipoprotein Fraction

Plasma triacylglycerol-rich lipoprotein fraction was prepared by ultracentrifugation of 3 mL plasma at a density of 1.063 g/mL for 19 hr at 105 000×g at 15° C. The tubes were sliced, and the floating fraction in the top 1 mL of each tube was harvested. The fraction was then dialyzed against 150 mmol/L sodium chloride, 16 mmol/L sodium phosphate and 4 mmol/L-potassium phosphate, pH 7.4, saturated with nitrogen.

Real-Time Quantitative RT-PCR

Total RNA was purified using Trizol (Gibco BRL), and 1 □g total RNA was reversed-transcribed in a total volume of 100 μl by use of a Reverse transcriptase kit (Applied Biosystems). Reactions in which RNA was omitted served as negative control, and reactions in which RNA was diluted served as standard curves.

Primers and Taqman probe for rat $\Delta^9$, $\Delta^6$ and $\Delta^5$ desaturases, peroxisome proliferator-activated receptor (PPAR)α and glyceraldehyde-3-phosphate dehydrogenase (GAPDH) were designed using Primer Express (Applied Biosystems). GAPDH and 18S rRNA were used as endogenous controls. Primers and Taqman probe for 18S rRNA were purchased from Applied Biosystems.

Real-time PCR was carried out in triplicate for each sample on an ABI 7900 sequence detection system (Applied Biosystems). For $\Delta^9$, $\Delta^□$ and $\Delta^5$ desaturases, PPAR□ and GAPDH, each 20 μl-reaction contained 3 μl first-strand cDNA, 1× Universal Master Mix (Applied-Biosystems), 300 nmol/L of each forward and reverse primer, and 250 nmol/L Taqman probe. For 18S rRNA the reaction contained 3 μl first-strand cDNA, 1× Universal Master Mix (Applied Biosystems), and 1×18S probe/primer reaction mix. All reactions were carried out using the following cycle parameters: 50° C. for 2 min and 95° C. for 10 min, followed by 40 cycles of 95° C. for 15 sec and 60° C. for 1 min, as generally recommended by Applied Biosystems. Ct readings (treshold cycle number) for each of the unknown samples were used to calculate the amount of desaturases, PPAR□ and GAPDH 4 and 18S rRNA. For each sample, results were normalised to GAPDH and 18S rRNA. Only results normalised to GAPDH are shown, but this was similar to the results normalised to 18 S rRNA.

The results are reported as means±SEM from 6 animals in each experimental group. Statistical analysis was by one-way Anova Dunett's test (Prism, GraphPad).

Example 1

Preparation of Fish Protein Hydrolyzate

FPH was produced from fish flesh remnants on salmon bone frames after filleting. Frames without heads from freshly filleted Atlantic salmon (*Salmon salar*, L.) were taken directly from the production line and frozen at −20±2° C.: Within a week the frozen frames were Used in the enzymatic hydrolyzing process.

The enzymatic hydrolyzis was performed with Protamex™ at a pH of about 6.5 and at at temperature of 55±2° C. Protamex™ (E.C. 3.4.21.62/3.4.24.28) is a *Bacillus protease* complex from Novozymes AS (Bagsvaerd, Denmark) and fulfills the purity demands for food-grad enzymes. The ratio of salmon frames to water was 1.14. An enzyme to substrate ratio of 11.1 AU/kg crude protein was used in the hydrolysis. After 60 min of enzymic treatment the temperature was elevated to 98° C., which was reached after 105 min.

Large bones were retained in the hydrolysing tank, while small bones were removed by filtering the hydrolysate through a mesh. Thereafter the insoluble fraction was removed in a two-phase separator (Westfalia, Germany, SC.35-26-177, 15 kW, 7200 rpm), before the remaining mixture was separated in a three-phase separator (Westfalia, Germany, SB-7-36-+76, 4 kW, 8520 rpm) into salmon oil, emulsion fraction and aqueous fraction. The aqueous fraction fraction was concentrated (NitroAtomicer, Denmark, Falling Film Evaporator, Ff100), filtered through an ultramembrane with nominal molecular weight limit of 100 000 (PCI membrane systems. UK, PF100, 2.65 m$^2$) and finally the ultramembrane filtered fraction (UF fraction) was spray-dried (Niro Atomizer, Denmark, P-63 tower, $T_{in}$=200° C., $T_{out}$ 84° C.).

The UF fraction is termed fish protein hydrolyzate (FPH) and was used in experiments indicated below. The FPH material contains about 83% protein, 10% ash and about 2% lipids, based on dT weight. The amino acid compositions are given in table 2.

TABLE 2

Total amino acids in the UF fraction obtained by hydrolyses of salmon frames with Protamex ™.

| Component<br>Amino acids (g kg$^{-1}$ crude protein) | UF fraction |
|---|---|
| Arg | 59.4 ± 0.7 |
| His | 39 ± 1 |
| Ile | 27.5 ± 0.4 |
| Leu | 56.4 ± 0.1 |
| Lys | 63.7 ± 0.3 |
| Met | 22 ± 1 |
| Phe | 26.9 ± 0.7 |
| Thr | 39 ± 1 |
| Trp | 5.3 ± 0.1 |
| Val | 35.5 ± 0.4 |
| Ala | 74 ± 1 |
| Asn + Asp | 73 ± 3 |
| Cysteine (total) | 6.1 ± 0.7 |
| Gln + Glu | 116 ± 5 |
| Gly | 89 ± 3 |
| OH-Pro | 20.7 ± 0.7 |
| Pro | 47 ± 1 |
| Ser | 37 ± 2 |
| Tyr | 21 ± 2 |
| Tau | 6.2 ± .1 |

Example 2

FPH Induces a Plasma Cholesterol Lowering Effect

Obese Zucker rats were offered a diet containing 20% FPH as the sole source of protein. The FPH is a fatty acid free fish protein hydrolysate (FPH), produces as described above.

Figure 1:
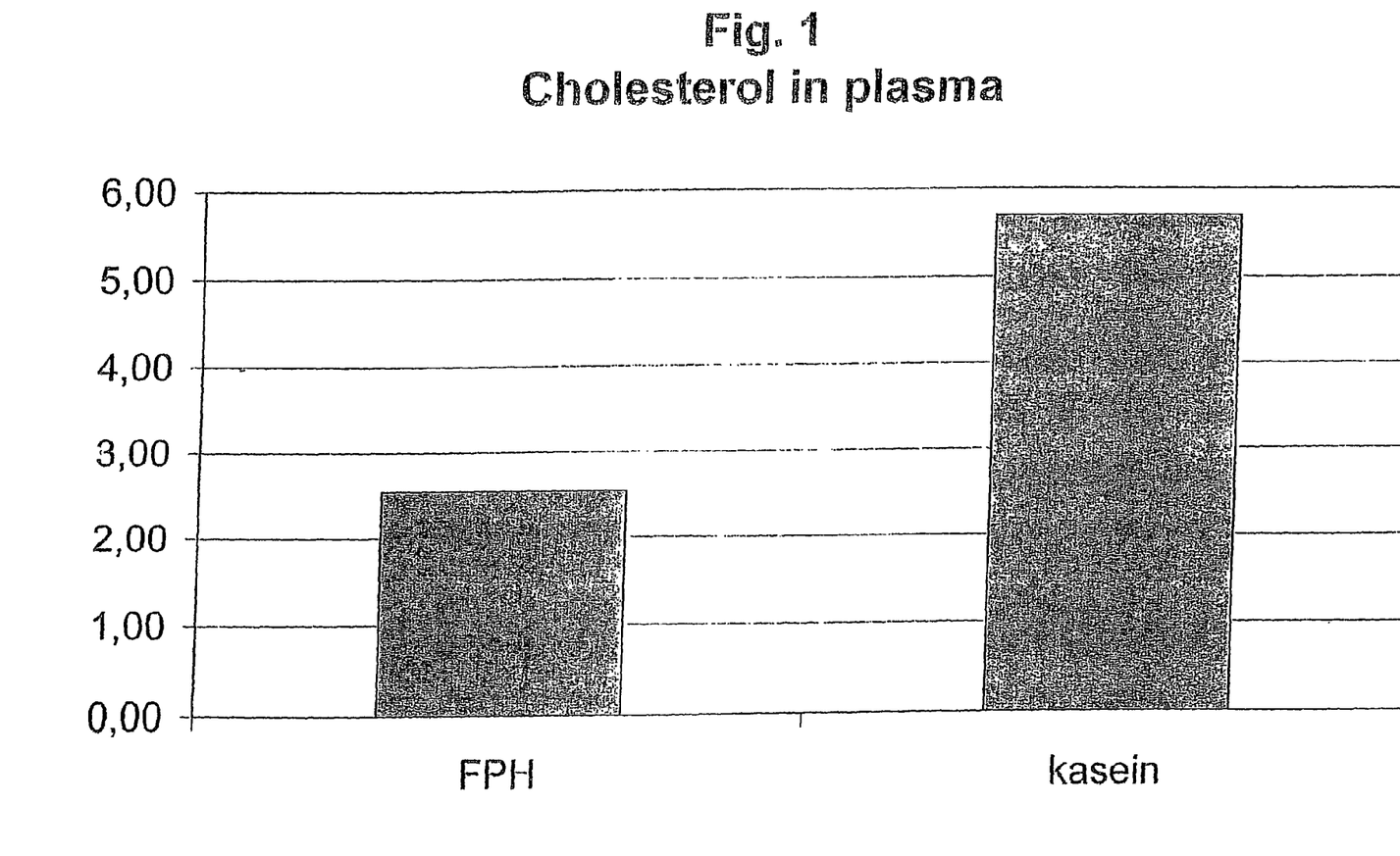
FIG. 1 shows that the enzyme treated fish protein hydrolysate (FPH) decreases the concentration of cholesterol in plasma.

The plasma cholesterol level were-reduced by 49% in Zucker rats fed FPH, as compared to rats fed casein as the feed protein. The result is shown in FIG. 1. The result clearly demonstrates that the FPH decreases the levels of cholesterol in the plasma and can be used as a cholesterol lowering agent.

Example 3

FPH Decreases the Concentration of Triacylglycerols in the Liver

Figure 2:
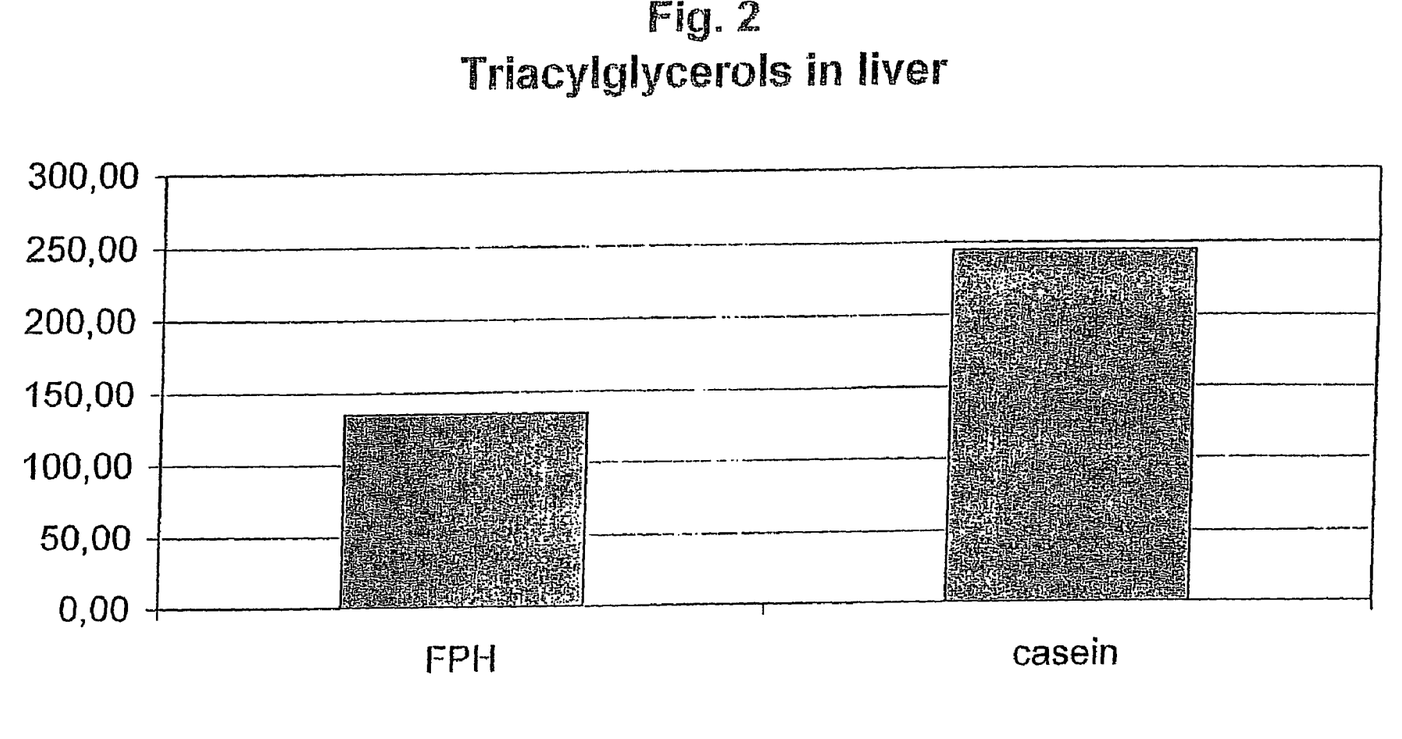
FIG. 2 shows that the enzyme treated fish protein hydrolysate (FPH) decreases the concentration of cholesterol in the liver.

FIG. 2 shows that FPH induces a lowering of the concentration of triacylglycerols (TG) in the liver of about 50%. This indicates that the compound of the present invention can be used as a lipid lowering agent, aid for the treatment and prevention of fatty liver.

Example 4

FPH Inhibits the Activity of Acyl-CoA: Cholesterol Acyltransferase

Acyl-CoA:cholesterol acyltransferase (ACAT) catalyses the reaction in which fatty acyl-CoA is esterified to cholesterol. Cholesteryl ester may then be stored in the cytoplasm as lipid droplets or be secreted as part of VLDL together with free cholesterol. Thus, ACAT plays a major role in the VLDL secretion and the subsequent cholesteryl ester accumulation and risk of cardiovascular disease. In the present Zucker rat experiment PFH protein changed the composition of lipid classes in the triacylglycerol-rich lipoprotein fraction, i.e. the cholesteryl ester and phospholipid contents were lower, while the triacylglycerol content was higher than in rats fed casein.

Figure 3:
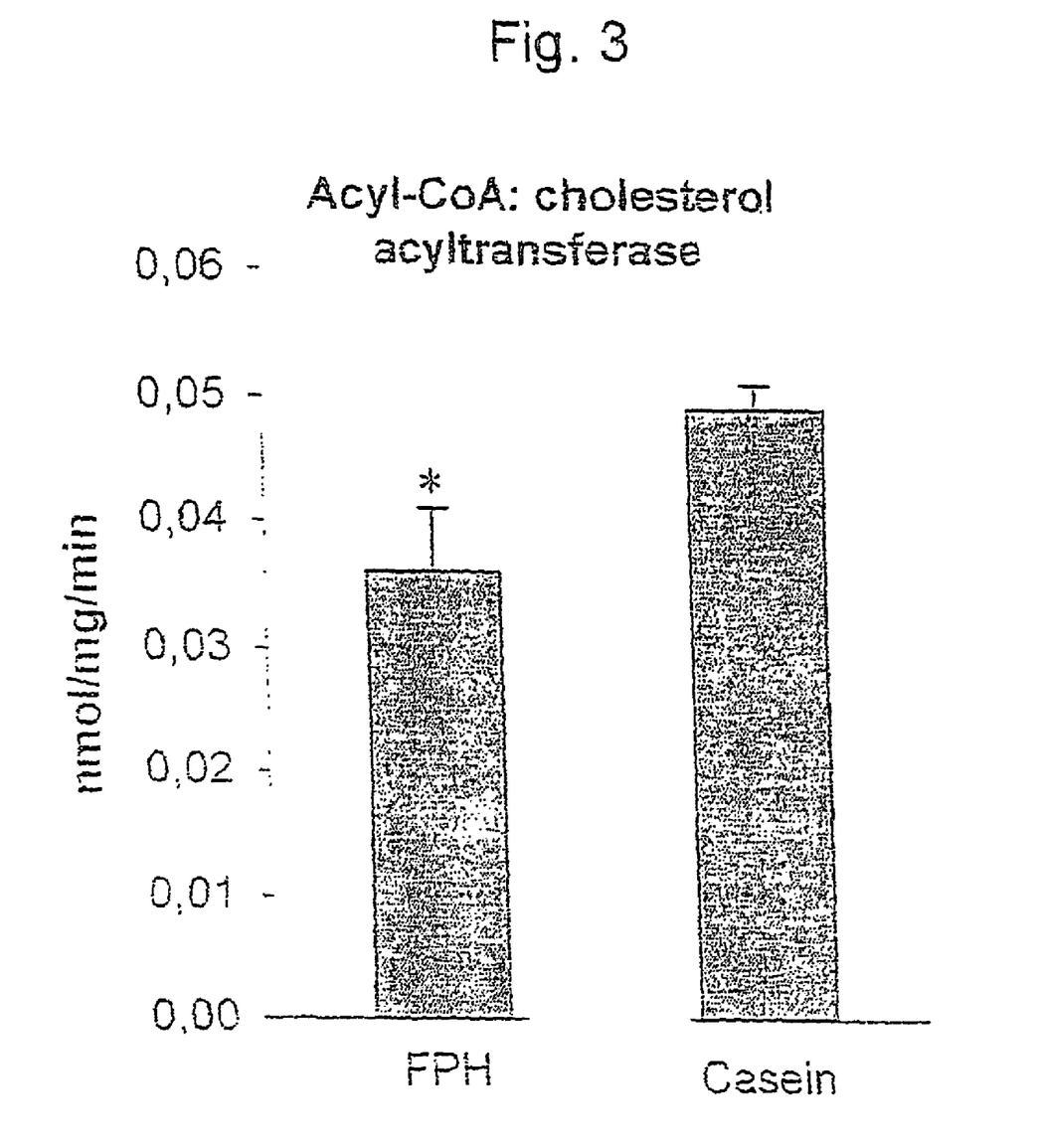
FIG. 3 shows that the enzyme treated fish protein hydrolysate inhibits the ACAT enzyme.

Furthermore, FIG. 3 shows that the ACAT activity decreased in rats fed FPH protein as compared to those fed casein. As there is strong evidence that increased ACAT activity plays an important role in the progression of atherosclerosis (46-49), this finding indicates that FPH and soy protein are cardioprotective.

FIG. 3 shows that ACAT activity was reduced about 30% in rats fed FPH as compared to Zucker rats fed casein.

Example 5

FPH Increases the Mitochondrial β-Oxidation

Figure 4:
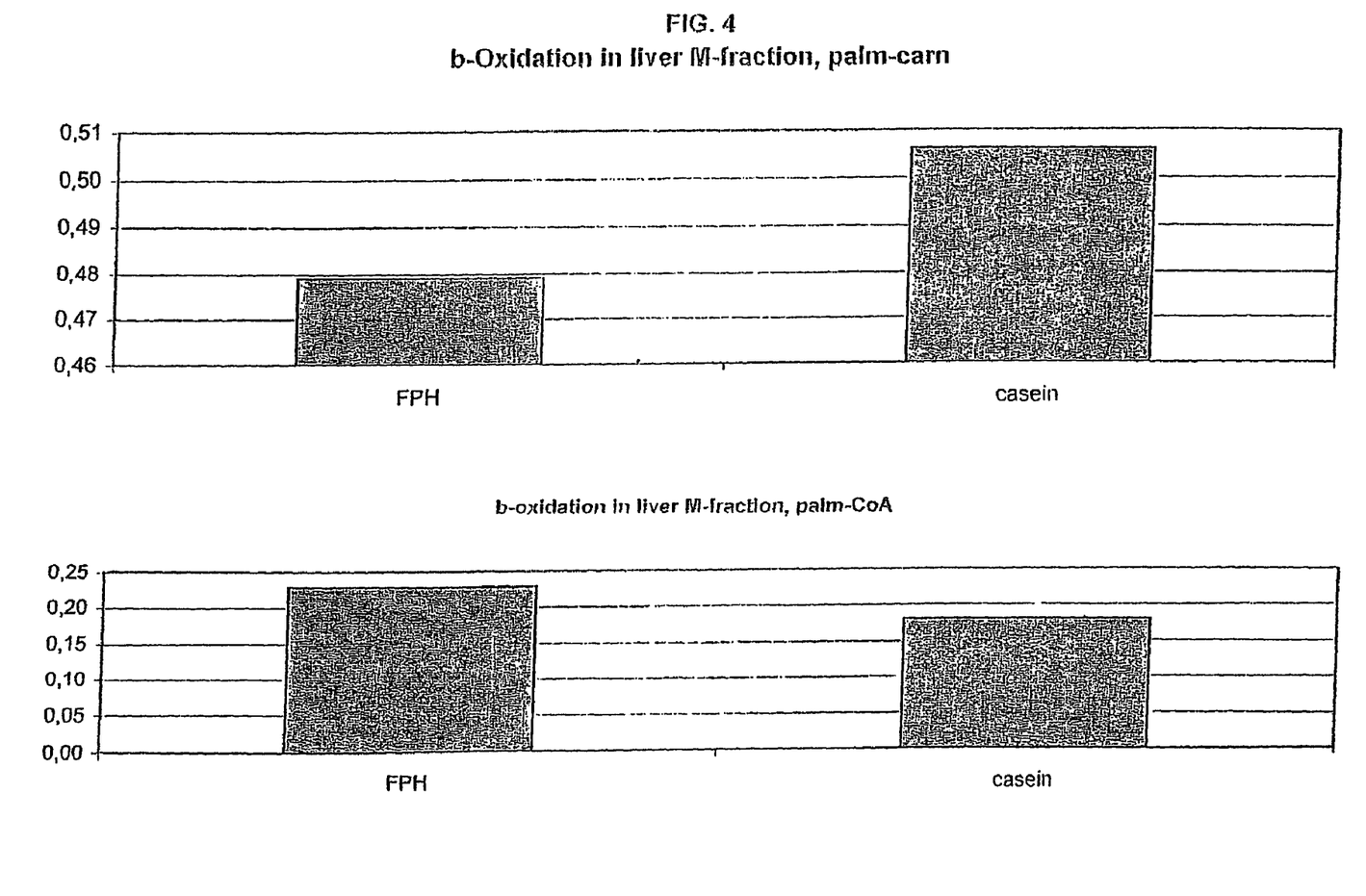
FIG. 4 shows that the enzyme treated fish protein hydrolysate increases the mitochondrial β-oxidation.

FIG. 4 shows that FPH increases the mitochondrial β-oxidation. Increased fatty acid oxidation is an important factor behind the lipid lowering effect of FPH. The increased fatty acid catabolism will decrease the amount of fatty acids available for esterification, and thereby reduce the production and secretion of VLDL by the liver. From FIG. 4 it can be seen that FPH significantly increased the oxidation of palmitoyl-CoenzymeA compared to control.

Example 6

FPH Interfere with the Lipid Homeostasis

The present data indicate that fat free FPH material interfere with the lipid homeostasis, and may promote accumulation of endogenous ligands for. In spite of an unchanged hepatic mRNA level of PPARα (data not shown), the fatty acid composition in liver, plasma and triacylglycerol-rich lipoprotein fraction were changed in rats fed FPH as compared to those fed casein, and the changes did not parallel in liver and plasma (Tables 3-5). The liver concentrations (Table 3) of the saturated 14:0 and 16:0 fatty acids were decreased, while 18:0 was increased in rats fed FPH, in particular those animals fed soy protein, as compared to those fed casein. The liver concentrations of monounsaturated fatty acids, including 18: ln-9, was decreased in rats fed FPH. As a result the 18:ln-9/18:0 ratio was reduced by 54 in rats fed FPH. The hepatic mRNA level of $\Delta^9$ desaturase, however, was not affected by the dietary protein (data not shown). In contrast to liver, an opposite effect was found in plasma on saturated and monounsaturated fatty acids (Table 4). In plasma, the saturated fatty acids 14:0 and 16:0 increased by FPH feeding. The monounsaturated fatty acids 18:ln-9 and 16:ln-7 increased 1.3-1.5 fold in rats fed FPH, and the ratio of 18:1 n-9 to 18:0 increased. In the triacylglycerol-rich lipoprotein fraction (Table 5) there were only minor changes in the saturated and monounsaturated fatty acids, i.e. 16:1n-7 in phospholipids was reduced in rats fed FPH and soy protein. The 18:1n-9/18:0 ratio was generally unchanged in the triacylglycerol-rich lipoprotein fraction. Of the n-6 fatty acids, 18:3n-6 was unchanged in liver, 18:2n-6 increased less than two-fold, while 20:3n-6 and 20:4n-6 increased several-fold with FPH. This resulted in a decrease in the 18:3n-6/18:2n-6 ratio, indicating a reduced $\Delta^6$ desaturation. The hepatic $\Delta^6$ desaturase mRNA expression was indeed reduced (data not shown). Furthermore, the 20:4n-6/20:3n-6 ratio was decreased, indicating a reduced $\Delta^5$ desaturation, in accordance with a decreased hepatic $\Delta^5$ desaturase mRNA level (data not shown). A two-fold increase in the 20:4n-6/18:2n-6 ratio and a 3- and 5-fold increase in the 20:4n-6/18:3n-6 ratio was seen in the animals fed the FPH. It is therefore anticipated that their hepatic elongase activities were increased. Animals fed FPH showed increased plasma concentrations of 18:2 n-6, while they showed decreased plasma concentrations of 20:4 n-6. As a result their 20:4n-6/18:2n-6 ratio in plasma was reduced by 54. Furthermore, the 20:4n-6/20:3n-6 ratio was decreased by 60% in FPH fed rats relative to those fed casein. In addition there was a tendency of decreased 18:3n-6/18:2n-6 and 20:4n-6/18:3n-6 ratios in animals fed FPH, although not significantly. In the triacylglycerol-rich lipoprotein fraction the fatty acid composition resembled the plasma profile, i.e. the 18:2n-6 increased and the 20:4n-6 decreased, resulting in reduced 20:4n-6/18:2n-6 (by 49-68%), 20:4n-6/18:3n-6 (by 53-65%) and 20:4n-6/20:3n-6 (by 35-37%) ratios in rats fed FPH. All of the n-3 fatty acids measured in liver were increased in both FPH fed rats. 18:3n-3 increased 1.8 in plasma by FPH feeding. 20:5n-3 was significantly increased in FPH-fed rats (44% increase), while DHA was reduced by FPH feeding (27% reduction). In the triacylglycerol-rich lipoprotein fraction the composition of the n-3 fatty acids pattern were changed only in phospholipids, where 20:5n-3 and 22:5n-3 were increased in rats fed FPH. This resembled the findings in plasma.

TABLE 3

Fatty acid composition in liver of Zucker rats fed FPH or casein for 3 weeks[1]

| Fatty acids | FPH | Casein |
|---|---|---|
| g/100 g fat | | |
| 14:0 | 1.5 ± 0.0* | 1.7 ± 0.1 |
| 16:0 | 35.2 ± 0.5* | 39.3 ± 0.6 |
| 18:0 | 8.8 ± 0.3* | 4.9 ± 0.3 |
| Amount saturated | 45.5 ± 0.7 | 45.9 ± 0.6 |
| 16:1n – 9 | 0.5 ± 0.0* | 0.8 ± 0.0 |
| 18:1n – 9 | 24.5 ± 0.7* | 29.6 ± 0.4 |
| 16:1n – 7 | 6.5 ± 0.3* | 8.1 ± 0.5 |
| 18:1n – 7 | 2.2 ± 0.2* | 3.0 ± 0.1 |
| Amount monounsaturated | 33.6 ± 0.9* | 41.5 ± 0.8 |
| 18:2n – 6 | 11.6 ± 0.1* | 8.8 ± 0.5 |
| 18:3n – 6 | 0.3 ± 0.0 | 0.4 ± 0.0 |
| 20:3n – 6 | 0.6 ± 0.1* | 0.1 ± 0.1 |
| 20:4n – 6 | 5.6 ± 0.4* | 2.1 ± 0.3 |
| Amount n – 6 | 18.1 ± 0.5* | 11.4 ± 0.8 |
| 18:3n – 3 | 0.6 ± 0.0* | 0.3 ± 0.0 |
| 20:5n – 3 | 0.3 ± 0.1 | n.d. |
| 22:5n – 3 | 0.4 ± 0.0 | n.d. |
| 22:6n – 3 | 1.4 ± 0.2* | 0.5 ± 0.1 |
| Amount n – 3 | 2.6 ± 0.2* | 0.8 ± 0.1 |
| Ratios | | |
| 18:1n – 9/18:0 | 2.8 ± 0.2* | 6.1 ± 0.3 |
| 18:3n – 6/18:2n – 6 | 0.028 ± 0.003* | 0.045 ± 0.003 |
| 20:4n – 6/18:2n – 6 | 0.5 ± 0.0* | 0.2 ± 0.0 |
| 20:4n – 6/18:3n – 6 | 18.0 ± 2.5* | 5.9 ± 1.1 |

[1]Values are means ± SEM, n = 6.
*different from casein, P < 0.05.
n.d., not detected.

TABLE 4

Fatty acid composition in plasma of Zucker rats fed FPH, or casein for 3 weeks[1]

| Fatty acids | FPH | Casein |
|---|---|---|
| g/100 g fat | | |
| 14:0 | 0.8 ± 0.1* | 0.6 ± 0.0 |
| 16:0 | 21.8 ± 1.0* | 18.6 ± 0.6 |
| 18:0 | 11.8 ± 0.5 | 12.6 ± 0.7 |
| Amount saturated | 33.3 ± 0.7 | 32.9 ± 0.8 |
| 16:1n – 9 | 0.4 ± 0.0 | 0.4 ± 0.0 |
| 18:1n – 9 | 13.6 ± 0.7* | 9.6 ± 0.5 |
| 16:1n – 7 | 4.0 ± 0.3* | 3.1 ± 0.1 |
| 18:1n – 7 | 1.6 ± 0.2 | 1.5 ± 0.1 |
| Amount monounsaturated | 18.5 ± 1.4 | 16.1 ± 1.1 |
| 18:2n – 6 | 22.0 ± 0.9* | 17.4 ± 1.0 |
| 18:3n – 6 | 0.7 ± 0.1 | 0.6 ± 0.1 |
| 20:3n – 6 | 1.3 ± 0.2 | 0.9 ± 0.2 |
| 20:4n – 6 | 17.1 ± 1.5* | 29.2 ± 1.1 |
| Amount n – 6 | 43.3 ± 1.9 | 46.3 ± 1.8 |
| 18:3n – 3 | 0.8 ± 0.1* | 0.5 ± 0.1 |
| 20:5n – 3 | 1.0 ± 0.1* | 0.6 ± 0.1 |
| 22:5n – 3 | 0.6 ± 0.0* | 0.4 ± 0.0 |
| 22:6n – 3 | 1.6 ± 0.1* | 2.3 ± 0.1 |
| Amount n – 3 | 4.0 ± 0.1 | 3.7 ± 0.1 |
| Ratios | | |
| 18:1n – 9/18:0 | 1.2 ± 0.1* | 0.8 ± 0.1 |
| 18:3n – 6/18:2n – 6 | 0.032 ± 0.004 | 0.037 ± 0.005 |
| 20:4n – 6/18:2n – 6 | 0.8 ± 0.1* | 1.7 ± 0.1 |
| 20:4n – 6/18:3n – 6 | 35.2 ± 7.4 | 41.6 ± 6.3 |
| 20:4n – 6/20:3n – 6 | 14.4 ± 2.2* | 37.6 ± 4.6 |

[1]Values are means ± SEM, n = 6.
*different from casein, P < 0.05.

TABLE 5

Fatty acid composition in the different lipid classes in the triacylglycerol-rich lipoprotein fraction of Zucker rats fed FPH or casein for 3 weeks[1]

| Fatty acids | Triacylglycerol | | Phospholipid | | Cholesteryl ester | |
|---|---|---|---|---|---|---|
| | FPH | Casein | FPH | Casein | FPH | Casein |
| g/100 g fat | | | | | | |
| 14:0 | 1.6 ± 0.1 | 1.5 ± 0.2 | 0.5 ± 0.1 | 0.5 ± 0.0 | 1.7 ± 0.2 | 1.2 ± 0.1 |
| 16:0 | 34.9 ± 3.0 | 33.4 ± 2.8 | 22.6 ± 0.2 | 24.7 ± 1.2 | 19.3 ± 2.1 | 19.0 ± 0.4 |
| 18:0 | 3.0 ± 0.4 | 3.2 ± 0.3 | 29.5 ± 0.7 | 27.3 ± 1.4 | 8.2 ± 1.1 | 5.4 ± 0.4 |
| Σ saturated | 39.9 ± 3.4 | 38.6 ± 3.2 | 54.8 ± 0.8 | 54.8 ± 0.3 | 32.0 ± 3.5 | 27.7 ± 0.8 |
| 16:1n − 9 | 0.5 ± 0.0 | 0.5 ± 0.1 | 0.1 ± 0.0 | 0.1 ± 0.0 | 0.6 ± 0.1 | 0.6 ± 0.0 |
| 18:1n − 9 | 26.0 ± 0.8 | 25.5 ± 1.0 | 5.7 ± 0.5 | 5.3 ± 0.3 | 11.8 ± 2.8 | 12.2 ± 1.8 |
| 16:1n − 7 | 6.0 ± 0.5 | 5.8 ± 0.7 | 0.7 ± 0.1 | 0.7 ± 0.0 | 4.6 ± 1.1 | 5.8 ± 1.0 |
| 18:1n − 7 | 2.6 ± 0.3 | 3.1 ± 0.2 | 1.0 ± 0.1* | 1.3 ± 0.1 | 1.0 ± 0.3 | 1.2 ± 0.3 |
| Σ monounsaturated | 35.5 ± 0.8 | 35.2 ± 1.7 | 7.9 ± 0.6 | 8.1 ± 0.2 | 18.5 ± 4.1 | 20.0 ± 3.0 |
| 18:2n − 6 | 19.4 ± 1.8 | 19.5 ± 4.3 | 20.4 ± 0.7 | 17.5 ± 1.1 | 17.7 ± 0.6* | 14.4 ± 0.2 |
| 18:3n − 6 | 0.3 ± 0.0 | 0.3 ± 0.0 | 0.1 ± 0.0 | 0.1 ± 0.0 | 1.3 ± 0.2 | 1.0 ± 0.2 |
| 20:3n − 6 | 0.4 ± 0.1 | 0.5 ± 0.1 | 1.8 ± 0.2 | 1.2 ± 0.2 | 1.0 ± 0.1* | 0.5 ± 0.1 |
| 20:4n − 6 | 1.1 ± 0.1 | 2.0 ± 0.4 | 10.8 ± 0.4* | 13.8 ± 0.7 | 27.0 ± 7.3 | 34.5 ± 3.5 |
| Σ n − 6 | 21.8 ± 2.0 | 23.0 ± 4.1 | 33.8 ± 0.8 | 33.2 ± 0.4 | 47.0 ± 7.2 | 50.4 ± 3.8 |
| 18:3n − 3 | 1.8 ± 0.0 | 1.5 ± 0.4 | 0.1 ± 0.0 | 0.1 ± 0.0 | 0.5 ± 0.1 | 0.5 ± 0.1 |
| 20:5n − 3 | 0.4 ± 0.1 | 0.4 ± 0.1 | 0.4 ± 0.0* | 0.1 ± 0.0 | 1.2 ± 0.3 | 0.6 ± 0.2 |
| 22:5n − 3 | 0.4 ± 0.0 | 0.4 ± 0.1 | 0.7 ± 0.1* | 0.5 ± 0.0 | n.d. | n.d |
| 22:6n − 3 | 0.4 ± 0.1 | 0.6 ± 0.1 | 2.3 ± 0.4 | 2.7 ± 0.0 | 0.7 ± 0.2 | 0.7 ± 0.0 |
| Σ n − 3 | 2.5 ± 0.8 | 3.0 ± 0.5 | 3.4 ± 0.4 | 3.5 ± 0.0 | 2.5 ± 0.3 | 1.8 ± 0.2 |
| Ratios | | | | | | |
| 18:1n − 9/18:0 | 8.9 ± 1.1 | 8.0 ± 0.5 | 0.2 ± 0.0 | 0.2 ± 0.0 | 1.4 ± 0.2* | 2.2 ± 0.2 |
| 18:3n − 6/18:2n − 6 | 0.018 ± 0.002 | 0.017 ± 0.006 | 0.004 ± 0.002 | 0.005 ± 0.001 | 0.071 ± 0.009 | 0.071 ± 0.014 |
| 20:4n − 6/18:2n − 6 | 0.058 ± 0.004 | 0.113 ± 0.032 | 0.5 ± 0.0* | 0.8 ± 0.1 | 1.5 ± 0.4 | 2.4 ± 0.2 |
| 20:4n − 6/18:3n − 6 | 3.3 ± 0.1* | 6.9 ± 1.0 | 92.3 ± 15.6 | 153.1 ± 13.7 | 21.2 ± 3.9 | 36.4 ± 8.7 |
| 20:4n − 6/20:3n − 6 | 2.8 ± 0.4* | 4.3 ± 0.2 | 6.0 ± 0.8* | 12.6 ± 2.1 | 27.5 ± 6.1* | 73.6 ± 11.2 |

[1]Values are means ± SEM, n = 3 (totally six rats, but plasma from two rats were pooled).
*different from casein, P < 0.05;
n.d., not detected;
soy, soy protein.

Example 7

FPH Lowers the Concentration of Homocystein in Plasma

Increased levels of homocysteine, i.e. hyperhomocysteinemia has been proposed to be associated with arterial diseases, and we thus measured the levels of homocysteine in the plasma samples from rats.

Total plasma homocysteine was measured by a fully automated fluorescence assay. 30 μl plasma was reduced by 30 μl NaBH4/DMSO solution (6 mol/L). After 1.5 min 20 μl of the fluorescence reagent monobromobimane (25 mmol/L) in acetonitrile was added and allowed to react for 3 min. 20 μl of the sample was then immediately analysed with HPLC by injection on a strong cation-exchange column, and then by column switching into a cyclohexyl silica column. The SCX column was eluted isocratically and the CH column was eluted with a linear methanol gradient (17-35% in 5 min) in 20 mmol/L formate buffer. The homocysteine was eluted at a retention time of 4.5 min. The results are given in table 5.

TABLE 5

Plasma concentration of homocysteine

| | Plasma concentration (μmol/L) |
|---|---|
| Control (casein) | 1.37 ± 0.27 |
| FPH | 1.17 ± 0.18 |

The invention claimed is:

1. A method of treating fatty liver, comprising administering to an animal in need of such treatment, a pharmaceutical or nutritional composition comprising, a Bacillus protease complex treated salmon protein hydrolyzate (FPH) material thereby lowering the concentration of plasma homocysteine and hepatic triacylglycerols of said animal.

2. The method of claim 1, wherein said animal is human.

3. The method of claim 1, wherein said animal is an agricultural animal selected from the group consisting of gallinaceous birds, bovine, ovine, caprine, and porcine.

4. The method of claim 1, wherein said animal is a domestic animal.

5. The method of claim 1, wherein said animal is a fish or shellfish.

6. The method of claim 1, wherein the nutritional composition is a food grade product or additive.

7. The method of claim 1, wherein said salmon flesh remnant on bone frames after filleting is treated with said enzyme.

8. A method of lowering the concentration of plasma homocysteine or hepatic triacylglycerols comprising administering to an animal in need of such, a pharmaceutical or nutritional composition comprising, a Bacillus protease complex treated salmon protein hydrolyzate (FPH) material thereby lowering the concentration of plasma homocysteine or hepatic triacylglycerols.

9. The method of claim 8, wherein the fish protein hydrolyzate material is obtained by a process comprising enzymatic treatment of fish material with said protease to obtain a hydrolyzate, filtration of the hydrolyzate, and spray-drying of ultramembrane filtered fraction of the hydrolyzate.

10. The method of claim 8, wherein the fish protein hydrolyzate material comprises about 83% protein, 10% ash and about 2% lipids, based on dry weight.

11. The method of claim 8, wherein the fish protein hydrolyzate material has an amino acid composition comprising about 59.4 grams arginine, 39 grams histidine, 27.5 grams isoleucine, 56.4 grams leucine, 63.7 grams lysine, 22 grams methionine, 26.9 grams phenylalanine, 39 grams threonine, 5.3 grams tryptophan, 35.5 grams valine, 74 grams alanine, 73 grams of combined asparagine and aspartate, 6.1 grams of total cysteine, 116 grams of combined glutamine and glutamate, 89 grams glycine, 20.7 grams hydroxy-proline, 47 grams proline, 37 grams serine, 21 grams tyrosine and 6.2 grams taurine, wherein said gram quantities of each amino acid are present as approximate amounts per kilogram of crude protein.

12. The method of claim 1, wherein the fish protein hydrolyzate material is obtained by a process comprising enzymatic treatment of fish material to obtain a hydrolyzate, filtration of the hydrolyzate, and spray-drying of an ultramembrane filtered fraction.

13. The method of claim 1, wherein the fish protein hydrolyzate material comprises about 83% protein, 10% ash and about 2% lipids, based on dry weight.

14. The method of claim 1, wherein the fish protein hydrolyzate material has an amino acid composition comprising about 59.4 grams arginine, 39 grams histidine, 27.5 grams isoleucine, 56.4 grams leucine, 63.7 grams lysine, 22 grams methionine, 26.9 grams phenylalanine, 39 grams threonine, 5.3 grams tryptophan, 35.5 grams valine, 74 grams alanine, 73 grams of combined asparagine and aspartate, 6.1 grams of total cysteine, 116 grams of combined glutamine and glutamate, 89 grams glycine, 20.7 grams hydroxy-proline, 47 grams proline, 37 grams serine, 21 grams tyrosine and 6.2 grams taurine, wherein said gram quantities of each amino acid are present as approximate amounts per kilogram of crude protein.

15. A method of treating hypercholesterolemia comprising administering to an animal in need of such treatment, a pharmaceutical or nutritional composition comprising, a Bacillus protease complex treated salmon protein hydrolyzate (FPH) material thereby lowering the concentration of plasma cholesterol.

16. A method of lowering the concentration of plasma cholesterol comprising administering to an animal in need of such treatment, a pharmaceutical or nutritional composition comprising, a Bacillus protease complex treated salmon protein hydrolyzate (FPH) material thereby lowering the concentration of plasma cholesterol.

* * * * *